US00PP25727P2

(12) United States Plant Patent
Hannink

(10) Patent No.: US PP25,727 P2
(45) Date of Patent: Jul. 21, 2015

(54) ***CLEMATIS* PLANT NAMED 'VITIWESTER'**

(50) Latin Name: ***Clematis* hybrid**
Varietal Denomination: Vitiwester

(71) Applicant: Johannes Antonius Jozef Hannink, Drunen (NL)

(72) Inventor: Johannes Antonius Jozef Hannink, Drunen (NL)

( * ) Notice: Subject to any disclaimer, the term of this patent is extended or adjusted under 35 U.S.C. 154(b) by 166 days.

(21) Appl. No.: 13/986,908

(22) Filed: Jun. 17, 2013

(51) Int. Cl.
*A01H 5/02* (2006.01)

(52) U.S. Cl.
USPC ..... Plt./228

(58) Field of Classification Search
USPC ..... Plt./228
CPC ..... A01H 5/02; A01H 5/00
See application file for complete search history.

(56) References Cited

PUBLICATIONS

Garden & Hardware News Oct./Nov. 2011 p. 43 and title page.*
Snoeijer. *Clematis* Nomenclatural Standards List 2010 v.1.01, retrieved on Jan. 15, 2015, retrieved from the Internet <wwwclematisinternational.com-nomstdlst2010vl> pp. 1-11.*
Upov Pluto Plant Variety 20150114 for *Clematis* 'Vitiwester', retrieved on Jan. 15, 2015, retrieved from the Internet <www3.wipo.int/pluto/user/en/index.jsp> one page.*

* cited by examiner

*Primary Examiner* — June Hwu
(74) *Attorney, Agent, or Firm* — Penny J. Aguirre

(57) ABSTRACT

A new cultivar of *Clematis* named 'Vitiwester', that is characterized by its deep red velvety flowers, its floriferous blooming habit, its typical *Viticella* Group type foliage, its height of 2 to 3 m, and its very good resistance to wilt.

2 Drawing Sheets

Botanical classification: *Clematis* hybrid.
Variety denomination: 'Vitiwester'.

BACKGROUND OF THE INVENTION

The present invention relates to a new and distinct cultivar of *Clematis* if hybrid origin (*Viticella* Group) and will be referred to hereafter by its cultivar name 'Vitiwester'. 'Vitiwester' is grown as an herbaceous climbing plant for use in the landscape or as a flowering potted plant for the terrace.

'Vitiwester' derived from an ongoing breeding program by the Inventor at his nursery in Drunen, The Netherlands. 'Vitiwester' was selected as a single unique plant in 2003 and arose from a controlled cross made in 2002 between an unnamed plant of *Clematis viticella* for the Inventor's breeding program as the female parent and *Clematis* 'Westerplatte' (not patented) as the male parent.

Asexual propagation of the new cultivar was first accomplished by internodial stem cuttings under the direction of the Inventor in Eindhoven, The Netherlands in 2010. Asexual propagation by internodal stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Vitiwester' as a unique cultivar of *Clematis*.

1. 'Vitiwester' exhibits deep red velvety flowers, a characteristic that is unique in the *Viticella* Group of *Clematis* known by the Inventor.
2. 'Vitiwester' exhibits a floriferous blooming habit.

3. 'Vitiwester' exhibits typical *Viticella* Group type foliage.
4. 'Vitiwester' reaches a height of 2 to 3 m (6 to 9 ft.).
5. 'Vitiwester' exhibits very good resistance to wilt.

The female parent of 'Vitiwester', an unnamed plant of *Clematis viticella* for the Inventor's breeding program, differs from 'Vitiwester' in having flowers that are blue-violet in color and smaller in size. The male parent of 'Vitiwester', 'Westerplatte', is similar to 'Vitiwester' in flower coloration. 'Westerplatte' differs from 'Vitiwester' in having larger flowers and foliage that is typical of large flowering hybrids of *Clematis*. 'Vitiwester' can be most closely compared to the cultivars 'Madame Julia Correvon' (not patented) and *Clematis viticella* 'Kermesina' (not patented). 'Madame Julia Correvon' differs from 'Vitiwester' in having flowers that are lighter and pinker in color that open more widely with tepals more separated, and in having a taller plant height. *Clematis viticella* 'Kermesina' differs from 'Vitiwester' in having flowers that are pinker in color with black anthers and in being much taller in height.

BRIEF DESCRIPTION OF THE DRAWINGS

The accompanying colored photographs illustrate the overall appearance and distinct characteristics of the new *Clematis*. The photographs were taken of three year-old plants of 'Vitiwester' as grown in a three-gallon container in Drunen, The Netherlands.

The photograph in FIG. 1 shows the plant and foliage habit of 'Vitiwester' in bloom.

Figure 1:
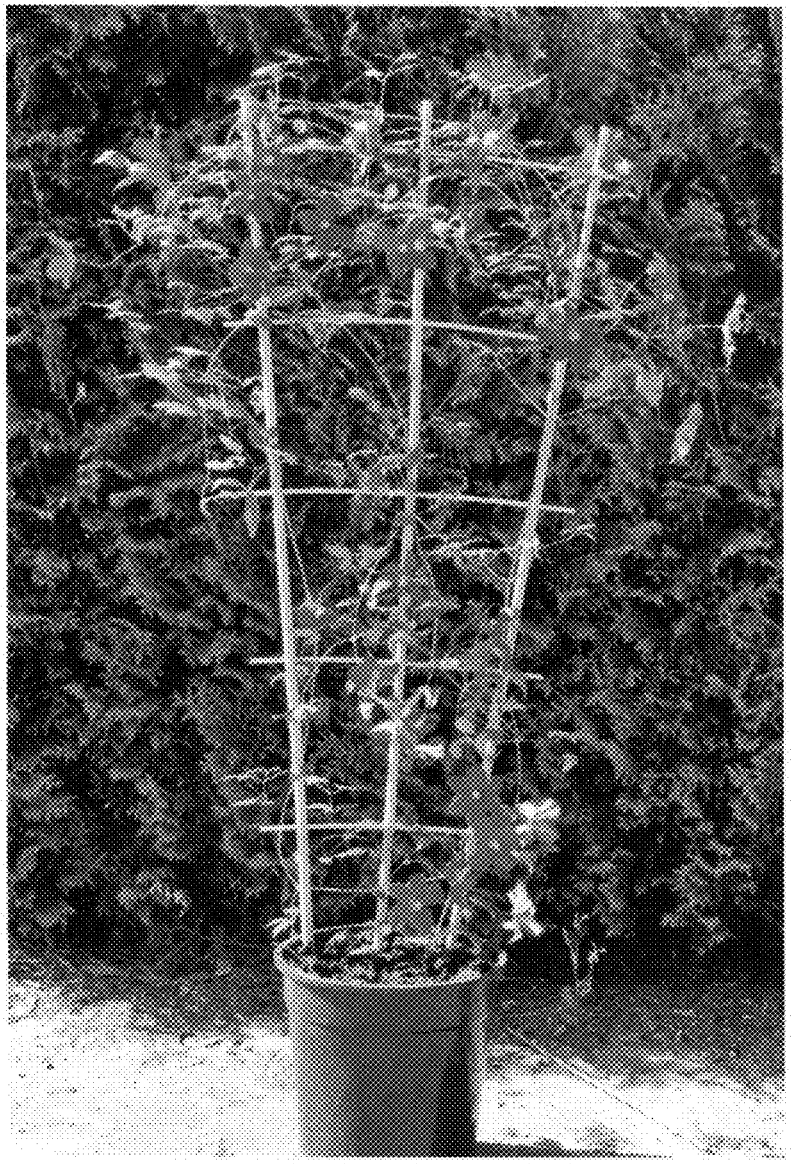
Figure 2:
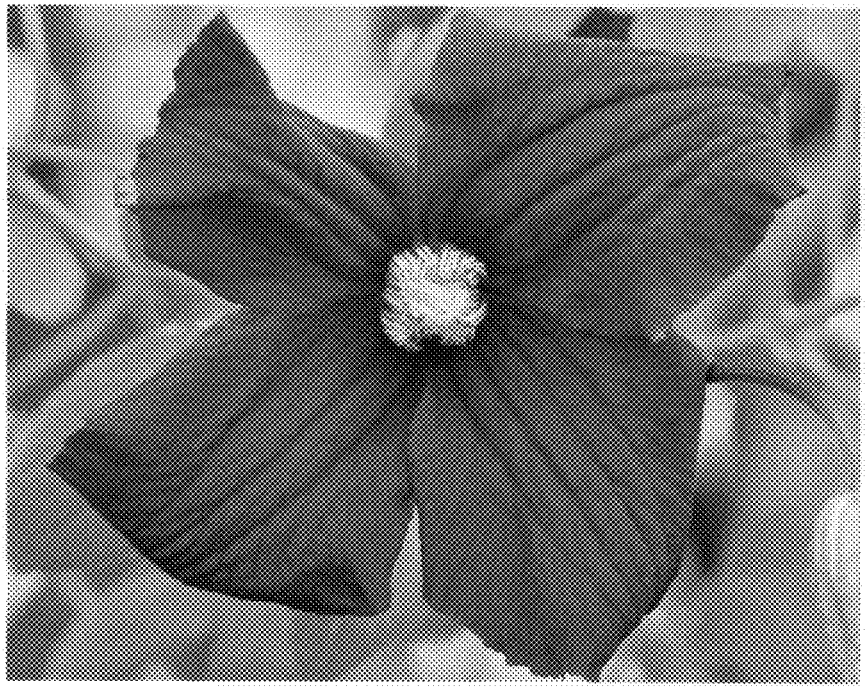

The photograph in FIG. 2 provides a close-up view of the upper side of a flower of 'Vitiwester'.

Figure 3:
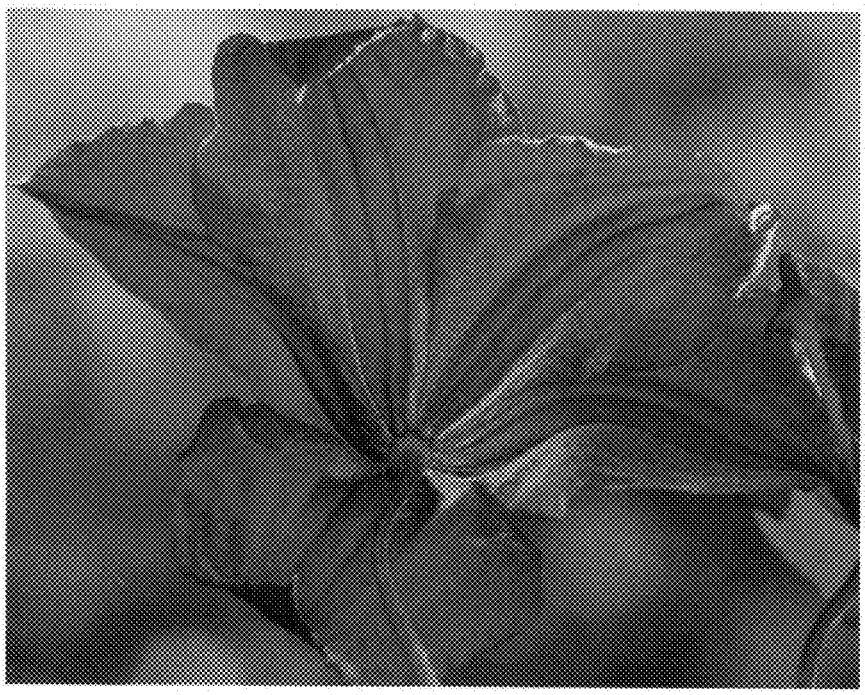

The photograph in FIG. 3 provides a close-up view of the lower side of a flower of 'Vitiwester'.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of three year-old plants of 'Vitiwester' as grown in three-gallon containers in Drunen, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from July to September in Drunen, The Netherlands.

*Plant type.*—Herbaceous vine, *Viticella* Group of *Clematis*.

*Plant habit.*—Climber, blooms on new wood.

*Height and spread.*—Three year-old plant is about 15 cm at base and reaches a height of 2 to 3 m (6 to 9 ft.).

*Cold hardiness.*—At least to U.S.D.A. Zone 4.

*Diseases.*—Has been observed to show very good resistance to wilt.

*Root description.*—Fleshy.

*Propagation.*—Internodial softwood cuttings from vegetative shoots.

*Growth rate.*—Moderate.

Stem description:

*Shape.*—Round and 6 ribbed.

*Stem color.*—New growth 138A, mature growth 177A.

*Stem size.*—Up to 91 cm in length and an average of 3 mm in width in width.

*Stem surface.*—Very sparsely pubescent with short hairs.

*Internode length.*—Average of 9 cm.

*Branching.*—Basal branching.

Foliage description:

*Leaf arrangement.*—Opposite.

*Leaf division.*—Biternate.

*Leaf attachment.*—Petiolate.

*Leaf size.*—Average of 9.5 cm in length and 9.5 cm in width.

*Leaflet shape.*—Ovate to broadly lanceolate.

*Leaflet base.*—Obtuse.

*Leaflet apex.*—Acute.

*Leaflet fragrance.*—None.

*Leaflet venation.*—Palmate, color matches leaf coloration.

*Leaflet margins.*—Entire.

*Leaflet attachment.*—Petioluled.

*Leaflet surface.*—Glabrous and dull on upper surface, glabrous and satiny on lower surface.

*Leaflet size.*—Average of 9.5 cm in length and 8.5 cm in width.

*Leaflet color.*—Young upper and lower surface; 137C, mature upper surface; 137B, mature lower surface; a color between 137B and 144A.

*Petioles.*—Average of 4 cm in length and 1 mm in width, 138A in color, sparsely pubescent surface.

*Petiolules.*—Average of 1.3 cm in length and 1 mm in width, 138A in color, sparsely pubescent surface.

Inflorescence description:

*Inflorescence type.*—Solitary; from one to 4 at upper axils.

*Inflorescence arrangement.*—Terminal and axillary on new growth.

*Peduncles.*—6 to 9 cm in length, a color between 145A and 147B in color and can be suffused with 187B, surface sparsely covered with short hairs at nodes.

*Peduncle bracts.*—Leaf-like, division simple, about 3 cm in length and 1.7 cm in width, color and surface is the same as leaflets.

*Bud description.*—Drooping, lanceolate in shape, about 3.5 cm in length and 2.1 cm in width, a blend of N77B and N77C in color with midribs of tepals N77B in color, pubescent surface.

*Flower fragrance.*—No.

*Lastingness of flowers.*—Individual flowers last about 7 days, the tepals are caducous followed by the stamens.

*Flower quantity.*—Solitary flowers, about 70 flowers are produced throughout the bloom season.

*Flower type.*—Single, rotate, spreading, star-shaped with very slightly overlapping tepals.

*Flower aspect.*—Upright to outward facing, flowers are slightly cupped (not fully open) and slightly reflexed near apex.

*Flower size.*—7.6 to 9 cm in diameter and about 2 cm in depth.

*Tepal number.*—4 to 6.

*Tepal shape.*—Broadly elliptic, flat in the cross section, and moderately recurved in the longitudinal section.

*Tepal apex.*—Acute with apiculate tip.

*Tepal base.*—Cuneate.

*Tepal margins.*—Wavy and slightly crenate.

*Tepal surface.*—Upper surface; glabrous and velvety, lower surface; pubescent, particularly on veins and margins.

*Tepal color.*—Upper surface; a blend of 59A through 59C, lower surface; a blend of 59A through 59C with pubescence 76A.

*Tepal size.*—Average of 4 cm in length and 2.6 cm in width.

Reproductive organs:

*Gynoecium.*—Numerous pistils (about 25), 1 cm in length, style is 145D in color and plumose at base, stigma is curled, about 5 mm in length and 155A in color, ovary is 145C in color with a hairy surface.

*Androcoecium.*—(About 40 stamens), filaments are an average of 6 mm in length and 1 mm in width, glabrous surface, and about 145A in color, anthers are 3 mm in length, linear in shape, 162A in color with connective 145A, glabrous, pollen was not observed.

*Seed.*—Seed head is an average of 1.6 cm in length and 2.5 cm in width, seed development was not observed, ovary 145C in color with shiny hairs, style plumose at base, 144C in color and 1.5 cm in length; stigma 144C in color and blushed with 165A.

It is claimed:

1. A new and distinct cultivar of *Clematis* plant named 'Vitiwester' as herein illustrated and described.

* * * * *